US00PP18422P2

(12) United States Plant Patent
Verwer

(10) Patent No.: US PP18,422 P2
(45) Date of Patent: Jan. 15, 2008

(54) ***DAHLIA* PLANT NAMED 'KARMA CHOC'**

(50) Latin Name: *Dahlia hybrida*
Varietal Denomination: Karma Choc

(75) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 11/524,447

(22) Filed: Sep. 20, 2006

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell
(74) *Attorney, Agent, or Firm*—C. A. Whealy

(57) ABSTRACT

A new and distinct cultivar of *Dahlia* plant named 'Karma Choc', characterized by its upright and somewhat outwardly spreading plant habit; freely branching habit; dark-colored foliage; decorative-type inflorescence form; large inflorescences with dark purple-colored ray florets; and good garden performance and postproduction longevity.

2 Drawing Sheets

Botanical designation: *Dahlia hybrida.*
Cultivar denomination: 'Karma Choc'.

BACKGROUND OF THE INVENTION

The present relates to a new and distinct cultivar of *Dahlia* plant, botanically known as *Dahlia hybrida,* and hereinafter referred to by the name 'Karma Choc'.

The new *Dahlia* is a product of a planned breeding program conducted by the Inventor in Lisse, The Netherlands. The objective of the breeding program is to create new cut flower *Dahlia* cultivars that have a freely flowering habit, decorative inflorescence form, attractive ray floret coloration, and good postproduction longevity.

The new *Dahlia* originated from a cross-pollination in Lisse, The Netherlands during 2001, of a proprietary selection of *Dahlia hybrida* identified as code number VD1-41, not patented, as the female, or seed, parent with the *Dahlia hybrida* cultivar Karma Naomi, disclosed in U.S. Plant Pat. No. 11,413, as the male, or pollen, parent. The new *Dahlia* was discovered and selected by the Inventor as a single flowering plant within the progeny of the stated cross-pollination in a controlled environment in Lisse, The Netherlands during the summer of 2002.

Asexual reproduction of the new *Dahlia* by cuttings since the spring of 2003 in a controlled environmental in Lisse, The Netherlands, has shown that the unique features of this new *Dahlia* are stable and reproduced true to type in successive generations.

SUMMARY OF THE INVENTION

The cultivar Karma Choc has not been observed under all possible environmental conditions. The phenotype may vary somewhat with variations in environment such as temperature and light intensity, without, however, any variance in genotype.

The following traits have been repeatedly observed and are determined to be the unique characteristics of 'Karma Choc'. These characteristics in combination distinguish 'Karma Choc' as a new and distinct cultivar of *Dahlia:*

1. Upright and somewhat outwardly spreading plant habit.
2. Freely branching habit.
3. Dark-colored foliage.
4. Decorative-type inflorescence form.
5. Large inflorescences with dark purple-colored ray florets.
6. Good garden performance and postproduction longevity.

Compared to plants of the female parent selection, plants of the new *Dahlia* differ primarily in ray floret coloration and plant size. Compared to plants of the male parent, the cultivar Karma Naomi, plants of the new *Dahlia* are most compact, flower earlier and have darker-colored ray florets.

Plants of the new *Dahlia* can be compared to plants of the *Dahlia* cultivar Arabian Night, not patented. In side-by-side comparisons conducted in Lisse, The Netherlands, plants of the new *Dahlia* differed from plants of the cultivar Arabian Night in the following characteristics:

1. Plants of the new *Dahlia* were larger and stronger than plants of the cultivar Arabian Night.
2. Plants of the new *Dahlia* were more freely branching than plants of the cultivar Arabian Night.
3. Plants of the new *Dahlia* had larger and darker-colored leaves than plants of the cultivar Arabian Night.
4. Plants of the new *Dahlia* were more freely flowering than plants of the cultivar Arabian Night.
5. Inflorescences of plants of the new *Dahlia* were longer lasting than inflorescences of plants of the cultivar Arabian Night.
6. Ray florets of plants of the new *Dahlia* were darker in color than ray florets of plants of the cultivar Arabian Night.

BRIEF DESCRIPTION OF THE PHOTOGRAPHS

The accompanying photographs illustrate the overall appearance of the new *Dahlia.* The photographs show the colors as true as it is reasonably possible to obtain in colored reproductions of this type. Colors in the photographs may differ slightly from the color values cited in the detailed botanical description which accurately describe the colors of the new *Dahlia*.

The photograph on the first sheet comprises a side perspective view of typical flowering plants of 'Karma Choc' grown in an outdoor nursery.

The photograph on the second sheet is a close-up view of a typical inflorescence of 'Karma Choc'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Lisse, The Netherlands during the summer in an outdoor nursery and under conditions and practices which approximate those generally used in commercial *Dahlia* production. During the production of the plants, day temperatures ranged from 15° C. to 30° C. and night temperatures ranged from 10° C. to 20° C. Plants were pinched one time about three to four weeks after planting. Measurements and numerical values represent averages for typical flowering plants. Plants were about four months old when the photographs and description were taken.

Botanical classification: *Dahlia hybrida* cultivar Karma Choc.

Parentage:

*Female, or seed, parent.*—Proprietary selection of *Dahlia hybrida* identified as code number VD1-41, not patented.

*Male, or pollen, parent.*—*Dahlia hybrida* cultivar Karma Naomi, disclosed in U.S. Plant Pat. No. 11,413.

Propagation:

*Type.*—By cuttings.

*Time to initiate roots, summer.*—About three days at temperatures of about 17° C.

*Time to initiate roots, winter.*—About four days at temperatures of about 17° C.

*Time to produce a rooted young plant, summer.*—About 12 days at temperatures of about 17° C.

*Time to produce a rooted young plant, winter.*—About 15 days at temperatures of about 17° C.

*Root description.*—Fine to fleshy; tuber development has not been observed.

*Rooting habit.*—Freely branching; dense.

Plant description:

*Plant form/growth habit.*—Upright to somewhat outwardly spreading; conical plant form. Freely basal branching with about eight lateral branches and inflorescences held above the foliage on strong peduncles; bushy and dense. Moderately vigorous growth habit.

*Plant height.*—About 100 cm.

*Plant diameter or spread.*—About 50 cm.

*Lateral branches.*—Length: About 80 cm. Diameter: Towards the base, about 3 cm; towards the apex, about 5 mm. Internode length: About 5 cm to 13 cm. Aspect: Erect to somewhat outwardly spreading. Strength: Strong. Texture: Smooth glabrous. Color: 146A tinted with 187A.

Foliage description:

*Arrangement.*—Leaves opposite; leaves may be single or compound with three or five leaflets.

*Shape.*—Ovate.

*Apex.*—Aristulate.

*Base.*—Attenuate.

*Margin.*—Serrate and divided; sinuses divergent.

*Length.*—Single leaves: About 8 cm. Compound leaves with three leaflets: About 18 cm. Compound leaves with five leaflets: About 24 cm.

*Width.*—single leaves: About 5 cm. Compound leaves with three leaflets: About 13 cm. Compound leaves with five leaflets: About 17 cm.

*Venation pattern.*—Pinnate.

*Texture, upper and lower surfaces.*—Smooth, glabrous.

*Color.*—Developing foliage, upper surface: 137A. Developing foliage, lower surface: 148B. Fully developed, upper surface: Close to 200A; venation, 187A. Fully developed, lower surface: Close to 148B; venation, 183B.

*Petiole length.*—Single leaves; About 5 mm. Compound leaves with three leaflets: About 3 cm. Compound leaves with five leaflets: About 5 cm.

*Petiole diameter.*—Single leaves: About 2 mm. Compound leaves with three leaflets: About 2 mm. Compound leaves with five leaflets: About 5 mm.

*Petiole texture, upper and lower surfaces.*—Smooth, glabrous.

*Petiole color, upper surfaces.*—187A.

*Petiole color, lower surface.*—183A.

Inflorescence description:

*Appearance.*—Rotate single inflorescence form with ray and disc florets. Inflorescences positioned above the foliage on strong peduncles. Inflorescences face upright to slightly outwardly. Freely flowering habit; about 40 inflorescences develop per plant. Inflorescences persistent. Inflorescences not fragrant.

*Time to flower.*—Plants flower continuously during the summer and autumn in The Netherlands.

*Post-production longevity.*—Good postproduction longevity; inflorescences maintain good substance for about 22 days on the plant and for about nine days as a cut flower.

*Inflorescence bud.*—Height: About 1.5 cm. Diameter: About 2.5 cm. Shape: Oblate. Color: Between 200A and 187A.

*Inflorescence size.*—Diameter: About 13 cm. Depth (height): About 5 cm. Disc diameter: About 1.3 cm. Receptacle height: About 2.2 cm. Receptacle diameter: About 3 cm.

*Ray florets.*—Length: About 5 cm. Width: About 2.3 cm. Shape: Ovate. Apex: Obtuse. Base: Attenuate. Aspect: Initially upright to roughly perpendicular to the peduncle to reflexed; flat or cupped. Texture, upper and lower surfaces: Smooth, glabrous; velvety. Number of ray florets per inflorescence: About 120 arranged in about 15 whorls. Color: When opening, upper surface: Darker than 187A. When opening, lower surface: 187A. Fully opened, upper surface: Darker than 187A; color becoming closer to 187C with development. Fully opened, lower surface: 187C; longitudinal stripes, 187A.

*Disc florets.*—Shape: Tubular; apex dentate. Length: About 1.3 cm. Diameter, apex: About 2 mm. Diameter, base: About 0.8 mm. Number of disc florets per inflorescence: about 30. Color: Immature: 178A. Mature: Apex: 200A. Mid-section: 178A. Base: 1D.

*Phyllaries.*—Quantity per inflorescence: About seven arranged in a single whorl. Length: About 1.6 cm. Width: About 9 mm. Shape: Ovate. Apex: Obtuse. Base: Attenuate. Margin: Entire. Texture, upper and lower surfaces: Smooth, glabrous; satiny. Color, upper surface: 137A; longitudinal stripes, 187B. Color, lower surface: 187A.

*Peduncles.*—Length: Terminal peduncle: About 30 cm. Fourth peduncle: About 22 cm. Seventh peduncle: About 12 cm. Diameter: Towards the base, about 2 cm; towards the apex, about 7 mm. Strength: Strong. Aspect: Erect to about 20° from vertical. Texture: Smooth, glabrous. Color: 187A.

*Reproductive organs.*—Androecium: Quantity per disc floret: Five. Anther shape: Linear. Anther length: About 2 mm. Anther color: 17B. Pollen amount: Moderate. Pollen color: 23A. Gynoecium: Quantity per ray or disc floret: One. Pistil length: About 4 mm. Stigma shape: Lanceolate. Stigma color: 17A. Style length: About 3 mm. Style color: 1D. Ovary color: 166B. Seeds: Seed development has not been observed.

Disease/pest resistance: Plants of the new *Dahlia* have not been shown to be resistant to pathogens and pests common to *Dahlia*.

Garden performance: Plants of the new *Dahlia* have exhibited good tolerant to rain and wind and have been observed to tolerate temperatures from about 0° C. to about 35° C.

It is claimed:

1. A new and distinct *Dahlia* plant named 'Karma Choc' as illustrated and described.

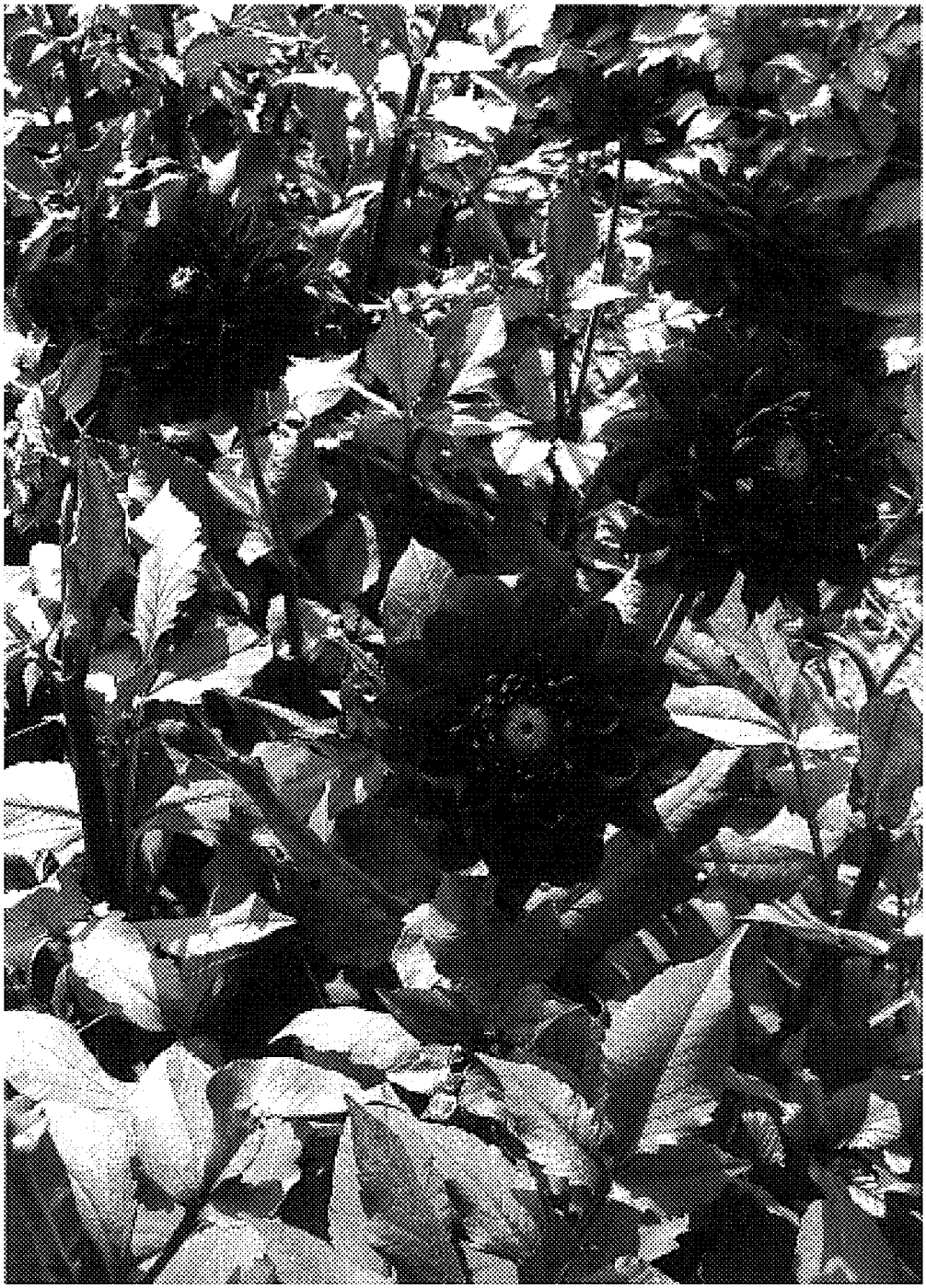

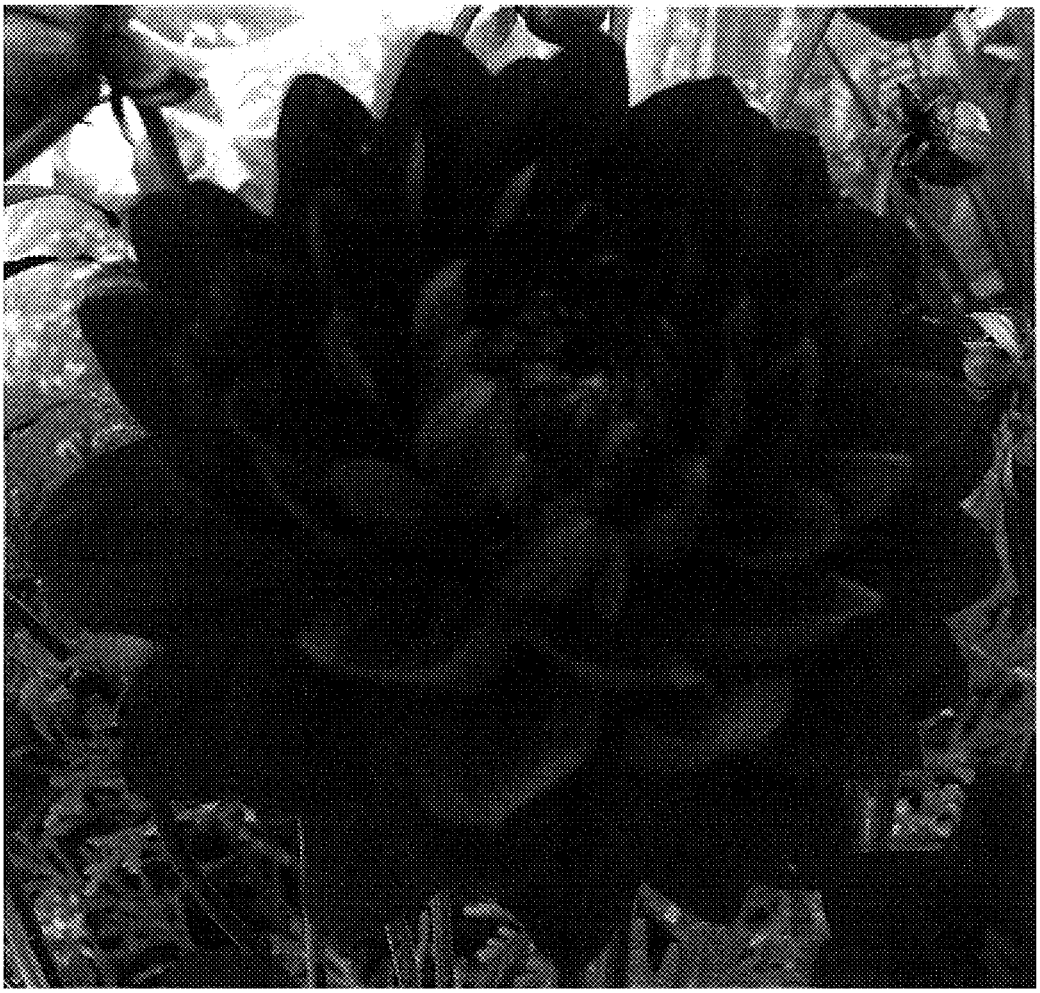

* * * * *